(12) United States Patent
Park et al.

(10) Patent No.: US 11,771,318 B2
(45) Date of Patent: Oct. 3, 2023

(54) METHOD FOR SUPPORTING READING OF FUNDUS IMAGE OF SUBJECT, AND DEVICE USING SAME

(71) Applicants: VUNO, INC., Seoul (KR); SEOUL NATIONAL UNIVERSITY HOSPITAL, Seoul (KR)

(72) Inventors: Sang Jun Park, Seoul (KR); Joo Young Shin, Seoul (KR); Jae Min Son, Gyeonggi-do (KR); Sang Keun Kim, Seoul (KR); Kyuhwan Jung, Seoul (KR); Hyun-Jun Kim, Gyeonggi-do (KR)

(73) Assignees: VUNO, INC., Seoul (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 281 days.

(21) Appl. No.: 16/759,594

(22) PCT Filed: Jul. 18, 2018

(86) PCT No.: PCT/KR2018/008099
§ 371 (c)(1),
(2) Date: Apr. 27, 2020

(87) PCT Pub. No.: WO2019/083129
PCT Pub. Date: May 2, 2019

(65) Prior Publication Data
US 2020/0288972 A1    Sep. 17, 2020

(30) Foreign Application Priority Data

Oct. 27, 2017 (KR) .......................... 10-2017-0141129
Oct. 27, 2017 (KR) .......................... 10-2017-0141130

(51) Int. Cl.
*A61B 3/12* (2006.01)
*G06T 7/11* (2017.01)
(Continued)

(52) U.S. Cl.
CPC .............. *A61B 3/1225* (2013.01); *A61B 3/12* (2013.01); *A61B 3/14* (2013.01); *G06T 7/0012* (2013.01);
(Continued)

(58) Field of Classification Search
CPC ............ G06T 7/11; G06T 7/0012; A61B 3/12
See application file for complete search history.

(56) References Cited

U.S. PATENT DOCUMENTS 5,868,134 A    2/1999 Sugiyama et al.
8,787,638 B2 *  7/2014 Zee .......................... A61B 3/12
                                          382/128
(Continued)

FOREIGN PATENT DOCUMENTS

CA    2910932 A1 * 11/2014  ........... A61B 3/0008
CN    106408562 A  * 2/2017  ........... G06T 7/0012
(Continued)

OTHER PUBLICATIONS

Machine translation of KR20130023735A (Year: 2013).*
(Continued)

*Primary Examiner* — John Villecco
*Assistant Examiner* — Courtney Joan Nelson
(74) *Attorney, Agent, or Firm* — IP & T GROUP LLP

(57) ABSTRACT

The present invention relates to a method for supporting reading of a fundus image of a subject, and a computing device using the same. Specifically, the computing device according to the present invention acquires the fundus image of the subject, extracts attribute information from the fundus image on the basis of a machine learning model for extract-
(Continued)

ing the attribute information of the fundus image, and provides the extracted attribute information to an external entity. In addition, when evaluation information on the extracted attribute information or modification information on the attribute information is acquired, the computing device according to the present invention can also update the machine learning model on the basis of the acquired evaluation information or modification information.

16 Claims, 12 Drawing Sheets

(51) Int. Cl.
*G06T 7/70* (2017.01)
*G16H 50/50* (2018.01)
*G16H 50/20* (2018.01)
*G16H 30/40* (2018.01)
*A61B 3/14* (2006.01)
*G06T 7/00* (2017.01)
*G06V 10/764* (2022.01)
*G06V 10/82* (2022.01)

(52) U.S. Cl.
CPC ............... *G06T 7/11* (2017.01); *G06T 7/70* (2017.01); *G06V 10/764* (2022.01); *G06V 10/82* (2022.01); *G16H 30/40* (2018.01); *G16H 50/20* (2018.01); *G16H 50/50* (2018.01); *G06T 2207/20084* (2013.01); *G06T 2207/30041* (2013.01)

(56) References Cited

U.S. PATENT DOCUMENTS

| | | | | |
|---|---|---|---|---|
| 9,008,391 | B1* | 4/2015 | Solanki | G06F 16/583 382/128 |
| 10,722,115 | B2* | 7/2020 | Celenk | G06V 10/82 |
| 2016/0192835 | A1* | 7/2016 | Matz | A61B 3/0025 351/246 |
| 2016/0345819 | A1* | 12/2016 | Jayasundera | A61B 3/0025 |
| 2017/0112372 | A1* | 4/2017 | Chakravorty | G06V 40/193 |

FOREIGN PATENT DOCUMENTS

| | | | | |
|---|---|---|---|---|
| EP | 2957219 | A1 * | 12/2015 | ........... A61B 3/0025 |
| JP | H7-136121 | A | 5/1995 | |
| JP | H9-313447 | H7 | 12/1997 | |
| JP | 2002-330951 | A | 11/2002 | |
| JP | 3479788 | B2 * | 12/2003 | ........... G06T 7/0012 |
| JP | 3630857 | B2 * | 3/2005 | ............ A61B 3/145 |
| JP | 2011-520503 | A | 7/2011 | |
| JP | 2013-501553 | A | 1/2013 | |
| JP | 2013-069076 | A | 4/2013 | |
| JP | 5203858 | B2 | 6/2013 | |
| JP | 2014-104275 | A | 6/2014 | |
| KR | 10-2013-0000576 | A | 1/2013 | |
| KR | 10-2013-0023735 | A | 3/2013 | |
| KR | 20130023735 | A * | 3/2013 | ............ A61B 5/055 |
| KR | 10-2014-0108417 | A | 9/2014 | |
| KR | 10-2015-0094080 | A | 8/2015 | |

OTHER PUBLICATIONS

Machine translation of JP-3630857-B2 (Year: 2005).*
Machine translation of JP-3479788-B2 (Year: 2003).*
Machine translation of CN-106408562-A (Year: 2017).*
Ronneberger O. et al., U-Net: Convolutional Networks for Biomedical Image Segmentation, http://lmb.informatik.uni-freiburg.de/, May 18, 2015.
Goodfellow I. J. et al., Generative Adversarial Nets, http://www.github.com/goodfeli/adversarial, Jun. 10, 2014.
Notice of Reasons for Refusal issued by the Japanese Patent Office dated Apr. 12, 2022.

* cited by examiner

[FIG. 1]
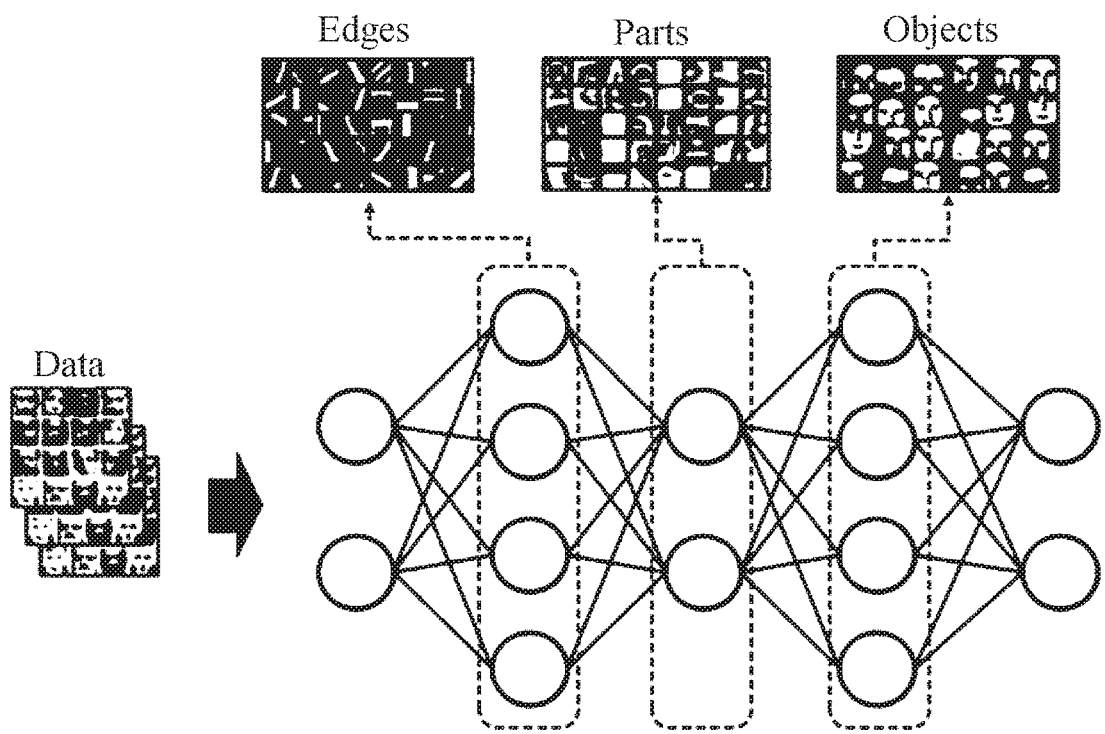
[FIG. 2]
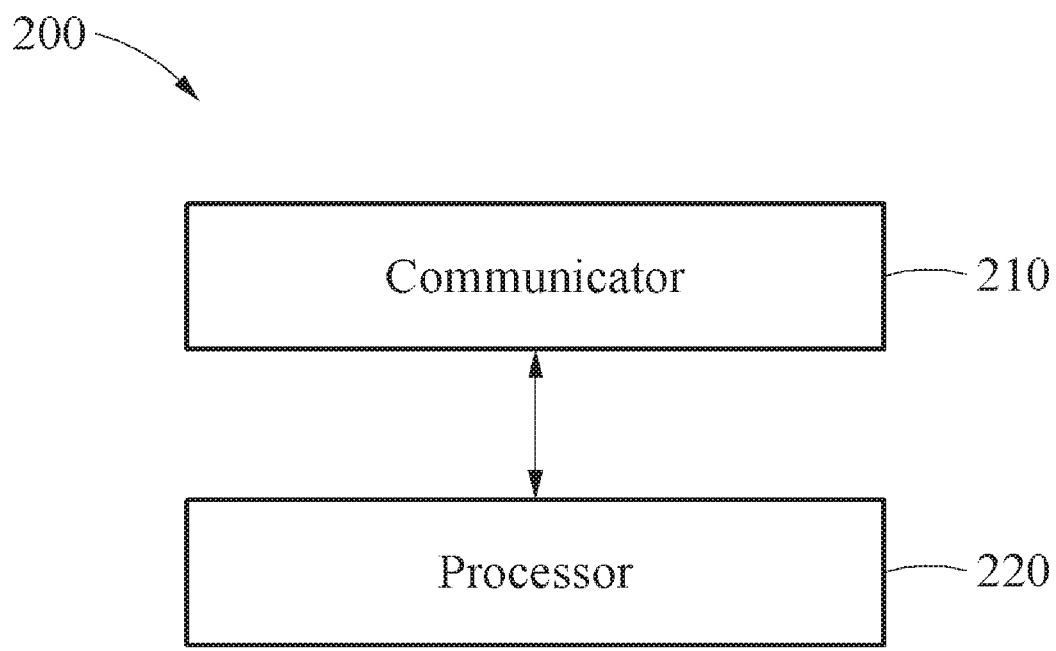

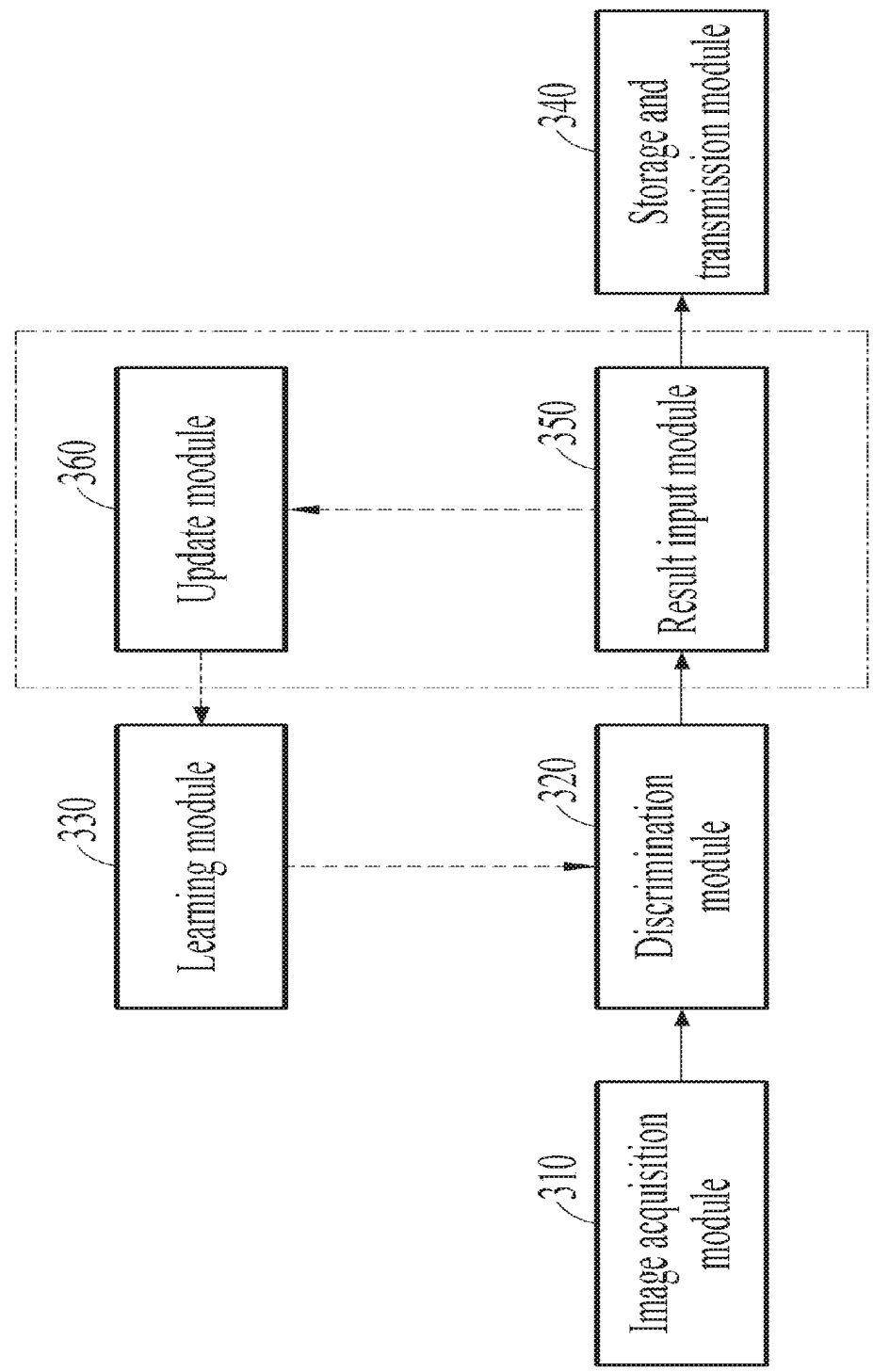
[FIG. 3]

[FIG. 4]
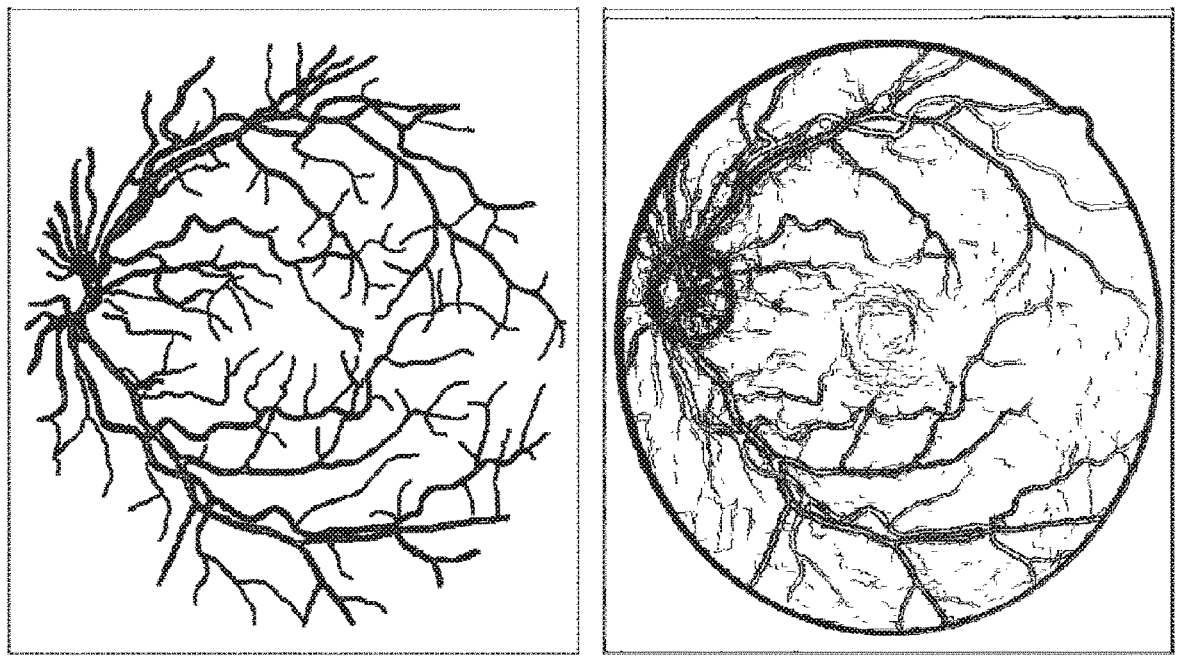
[FIG. 5]
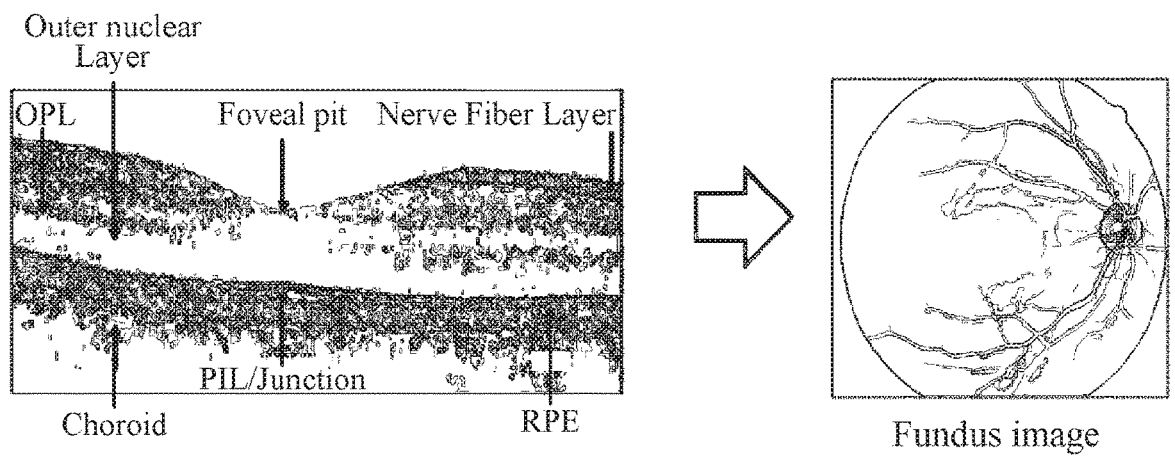
1. A spectral-domain optical coherence tomography(SD-OCT) section through the fovea of a healthy eye.
Conventional OCT image

[FIG. 6]

| Block | Input | Conv 1-4 | Conv 5 | Conv 6-9 | Output |
|---|---|---|---|---|---|
| Output size | (640,640,4) | $\left(\dfrac{640}{2^{n-1}}, \dfrac{640}{2^{n-1}}, 32*2^{n-1}\right)$ | $\left(\dfrac{640}{2^{n-1}}, \dfrac{640}{2^{n-1}}, 32*2^{n-1}\right)$ | $\left(\dfrac{640}{2^{9-n}}, \dfrac{640}{2^{9-n}}, 32*2^{9-n}\right)$ | (640, 640, 1) |
| Upsample | - | - | - | Conv n-1 | - |
| Skip-connect | - | - | - | Conv 10-n | - |
| Operations | - | $\left\{\begin{array}{c}3\times 3 \text{ conv} \\ \text{batch-norm} \\ \text{ReLU}\end{array}\right\} \times 2$ <br> $2\times 2$ maxpool | $\left\{\begin{array}{c}3\times 3 \text{ conv} \\ \text{batch-norm} \\ \text{ReLU}\end{array}\right\} \times 2$ | $\left\{\begin{array}{c}3\times 3 \text{ conv} \\ \text{batch-norm} \\ \text{ReLU}\end{array}\right\} \times 2$ | $\left\{\begin{array}{c}1\times 1 \text{ conv} \\ \text{sigmoid}\end{array}\right\} \times 1$ |

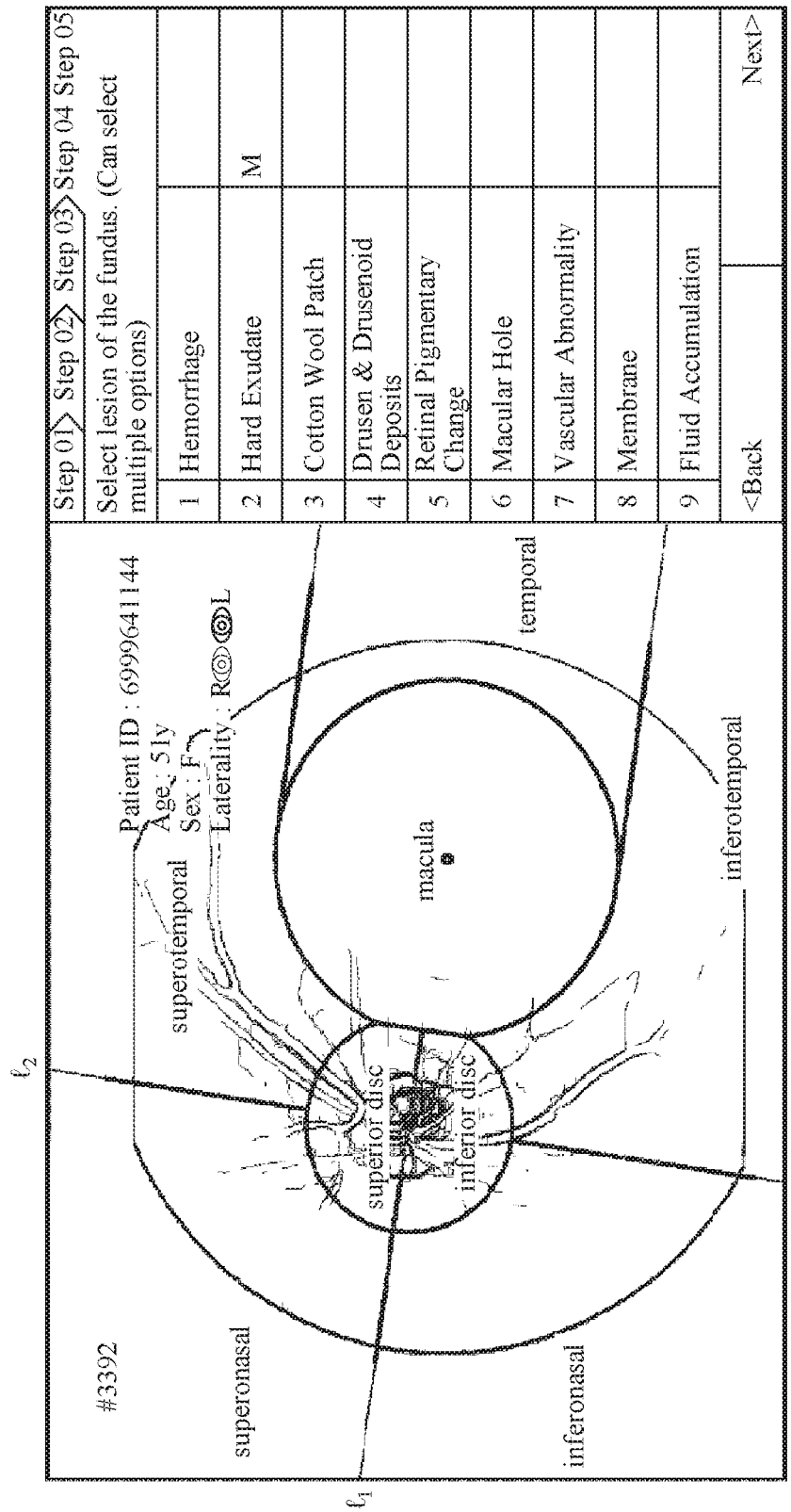
[FIG. 7]

[FIG. 8]
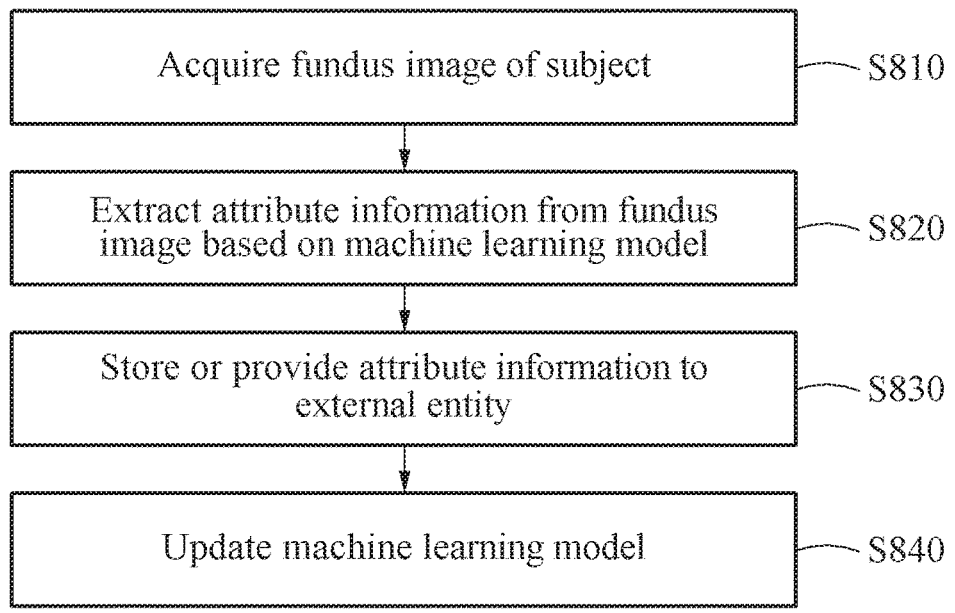
[FIG. 9]
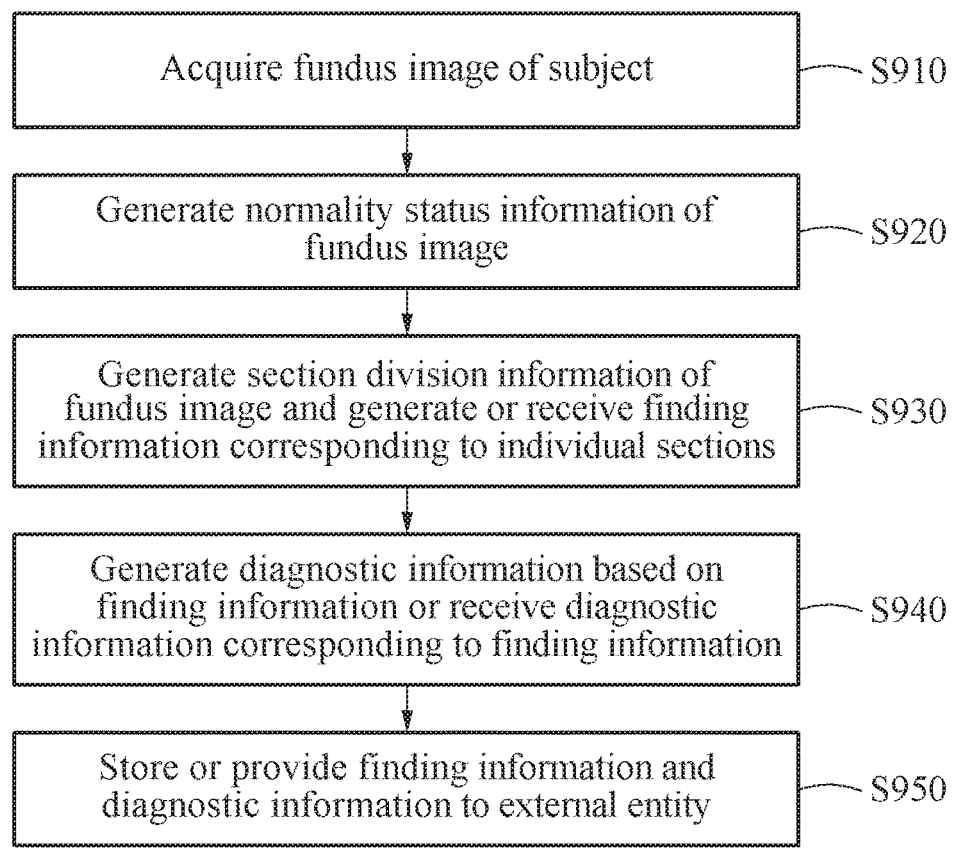

[FIG. 10A]
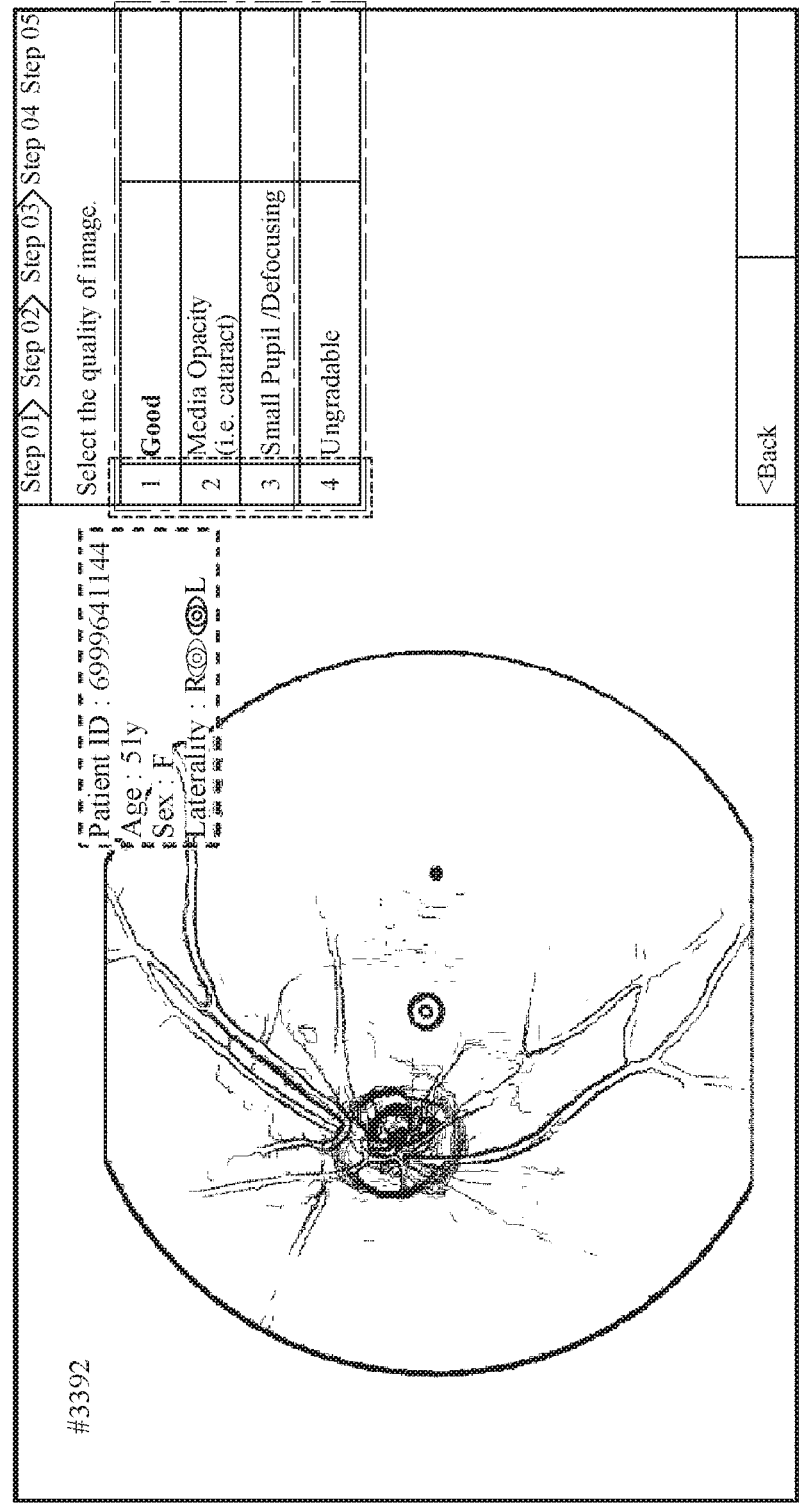

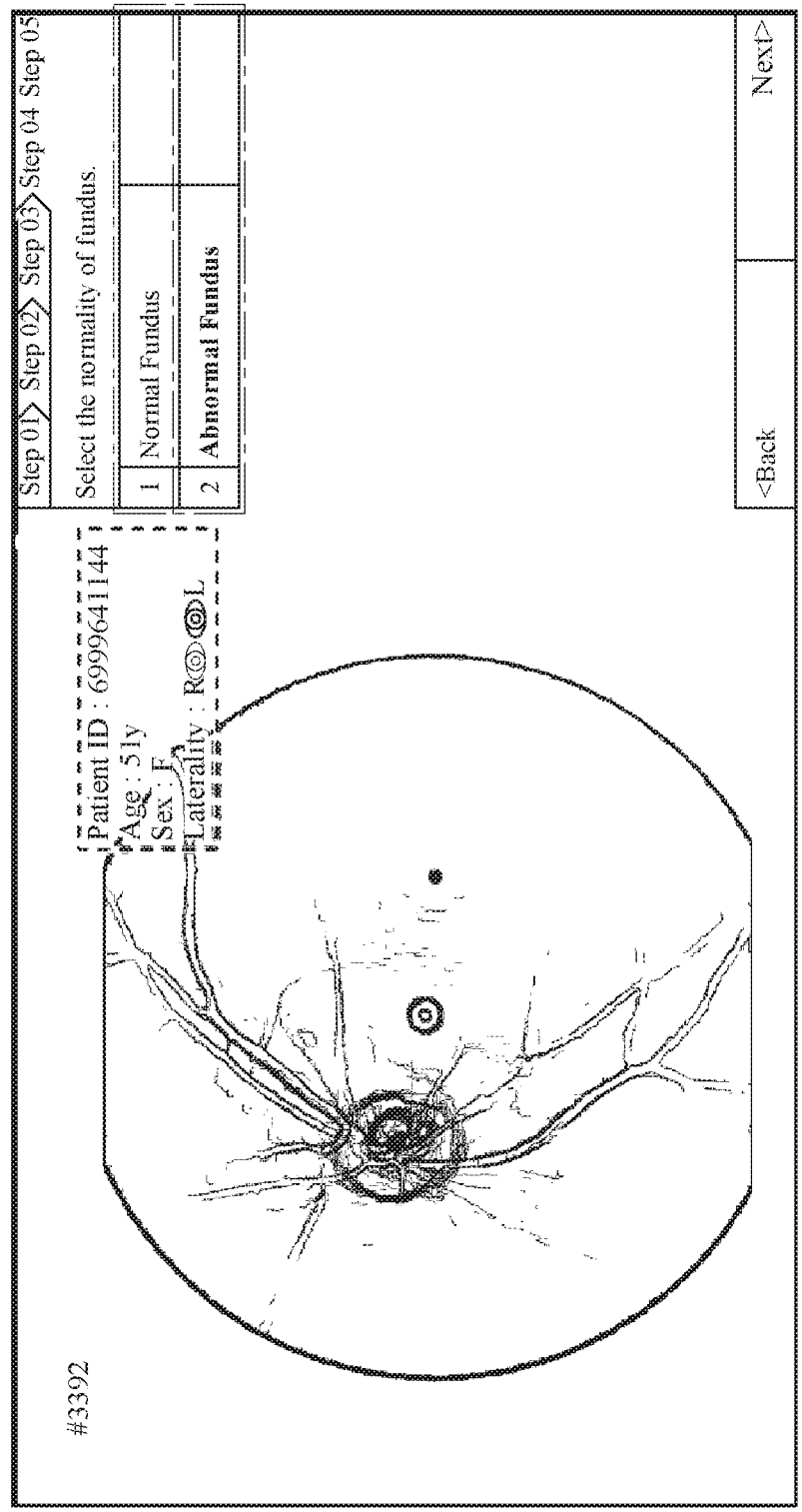
[FIG. 10B]

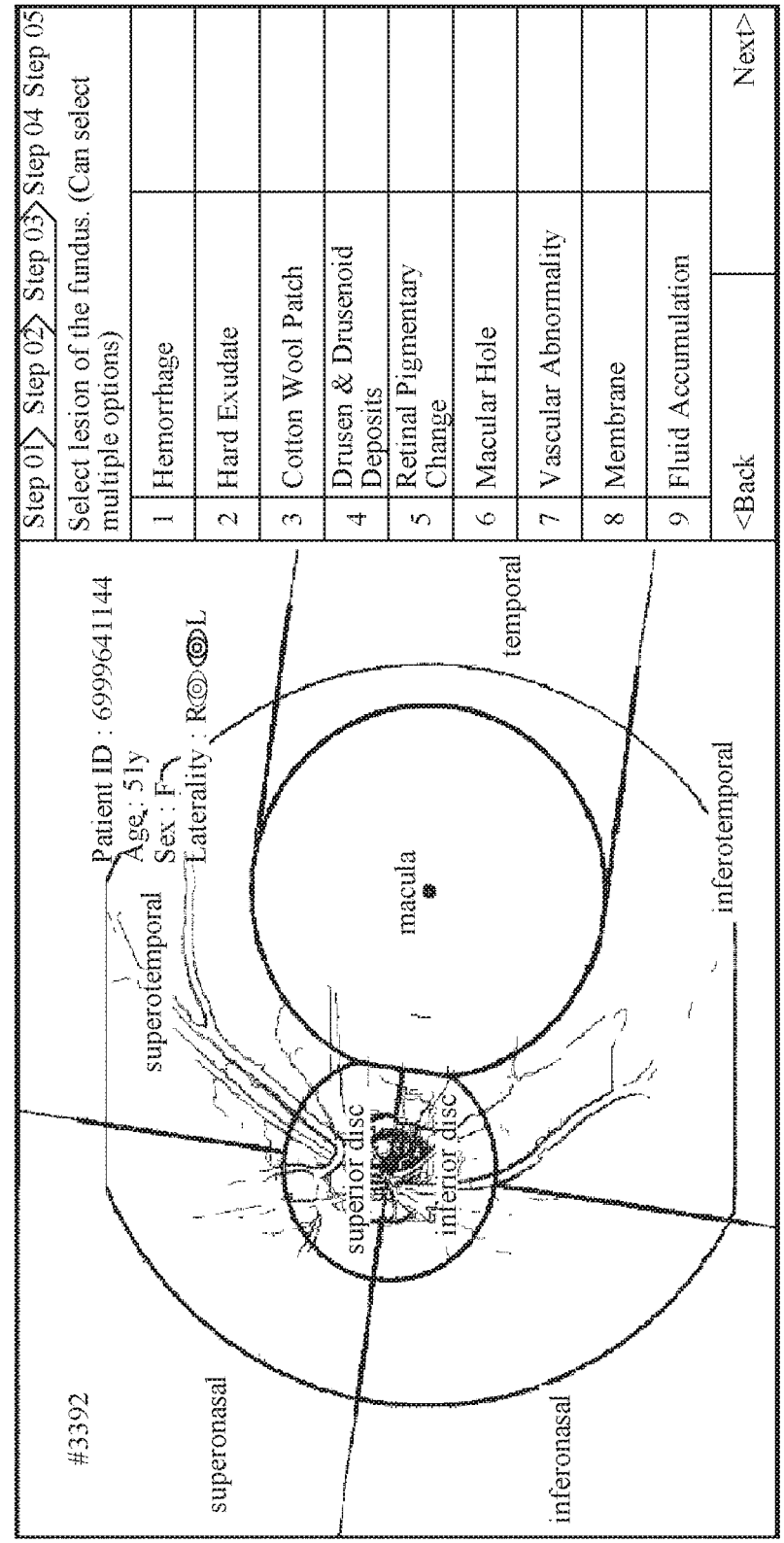
[FIG. 10C]

[FIG. 10D]
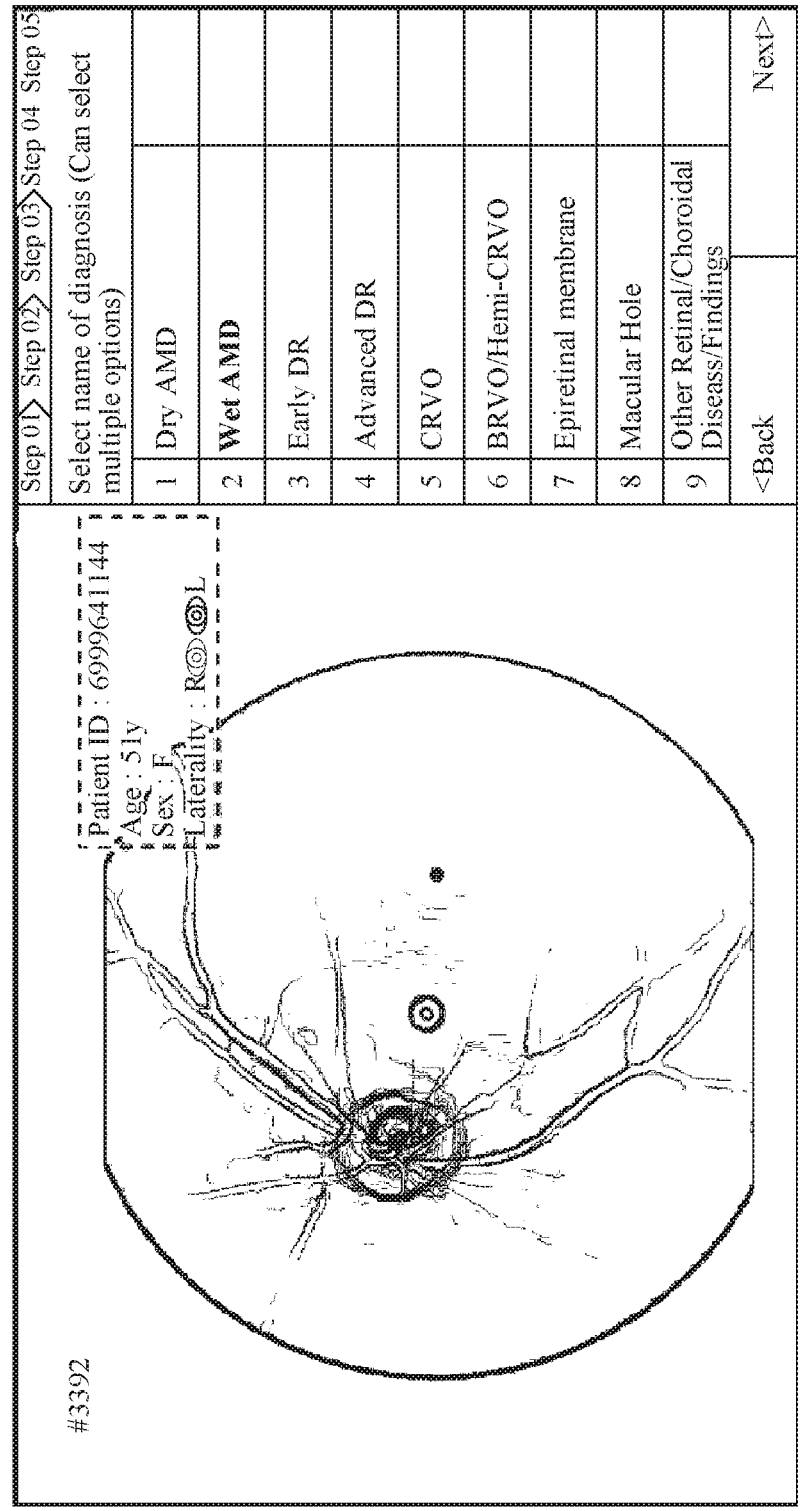

[FIG. 10E]
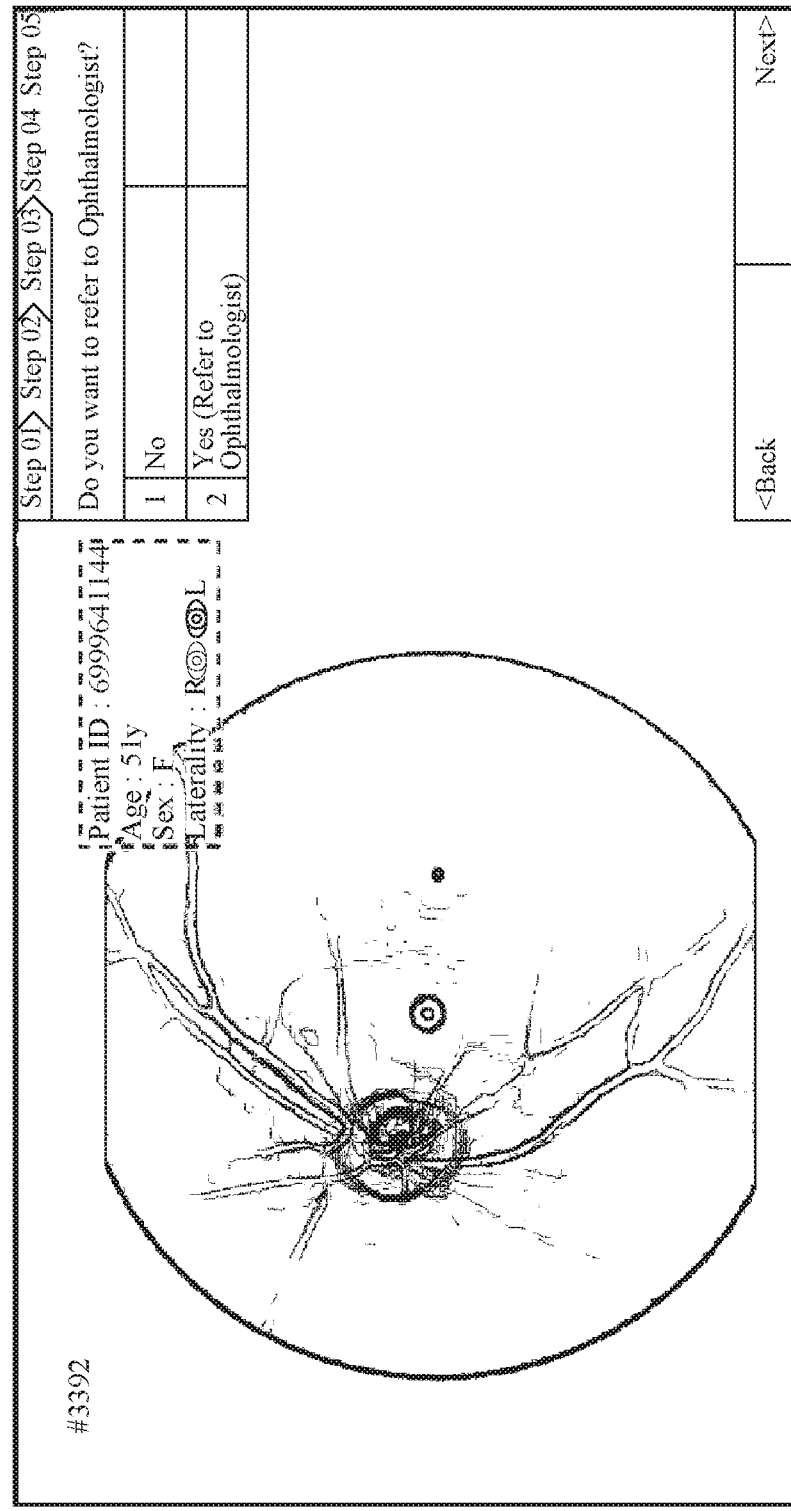

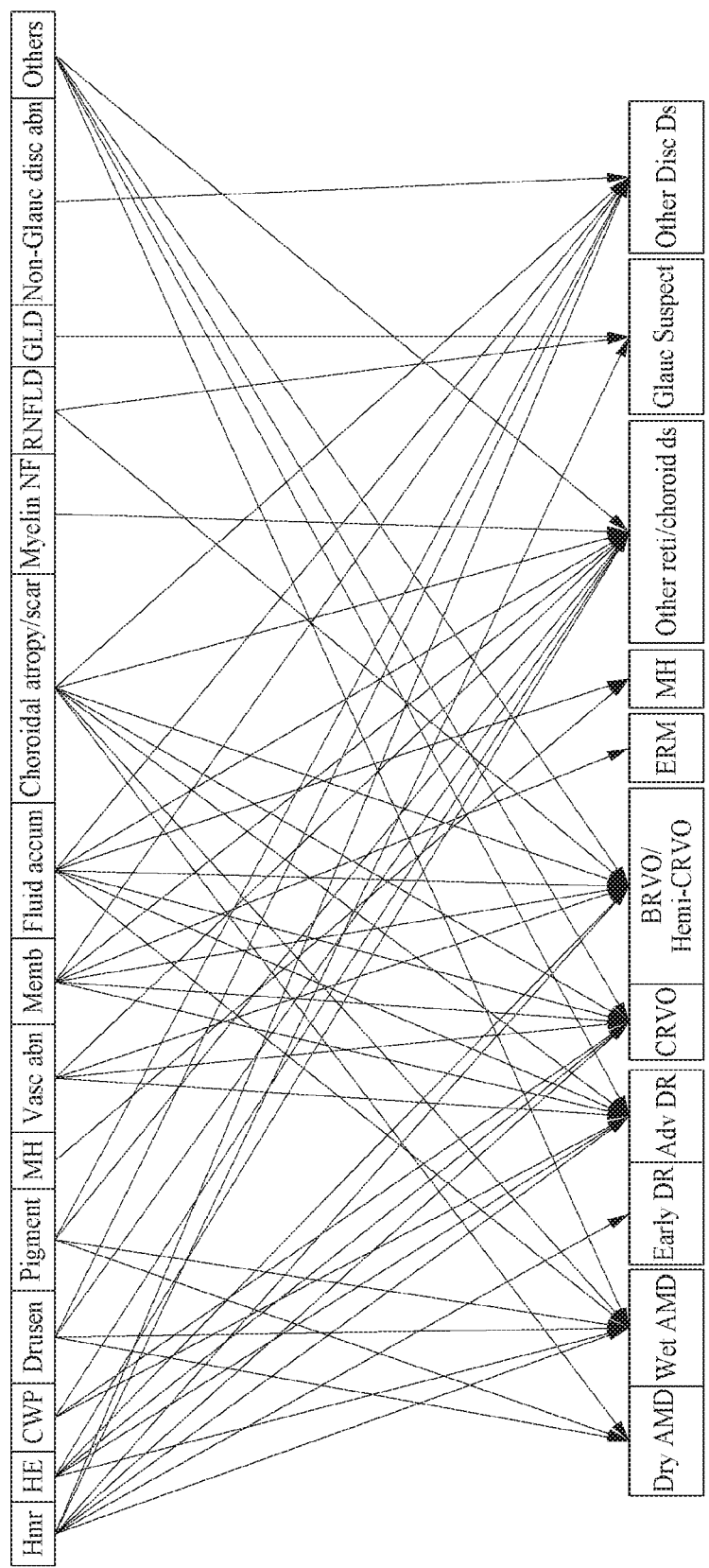
[FIG. 11]

METHOD FOR SUPPORTING READING OF FUNDUS IMAGE OF SUBJECT, AND DEVICE USING SAME

CROSS-REFERENCE TO RELATED APPLICATIONS

This application is a national stage application of PCT/KR2018/008099 filed on Jul. 18, 2018, which claims priority of Korean patent application numbers 10-2017-0141129 and 10-2017-0141130 filed on Oct. 27, 2017. The disclosure of each of the foregoing applications is incorporated herein by reference in its entirety.

TECHNICAL FIELD

The present disclosure relates to a method of supporting reading of a fundus image of a subject and a computing apparatus using the same. More particularly, the computing apparatus according to the present disclosure acquires the fundus image of the subject, extracts attribute information from the fundus image based on a machine learning model for extracting the attribute information of the fundus image, and provides the extracted attribute information to an external entity. Also, when evaluation information on the extracted attribute information or modification information of the attribute information is acquired, the computing apparatus may update the machine learning model based on the evaluation information or the modification information.

RELATED ART

A fundus image may be frequently used for reading at ophthalmology since abnormalities of the retina, optic nerve, and macula portion are observable. Here, a conventional labeling system provided for reading the fundus image is inefficient or ineffective in the following aspects.

Initially, the conventional labeling system does not consider logical relationships between selection items and accordingly, may perform unnecessary or unreasonable labeling. In detail, pathologically impossible labeling may be allowed since exclusive relationships between diseases are not considered.

Also, the conventional labeling system may use a finding and diagnosis together and thus, may not effectively manage data. Also, a section setting for displaying a position corresponding to the finding does not apply a structural characteristic of an eye.

Accordingly, proposed are herein a method of supporting reading of a fundus image to solve the aforementioned issues and to allow the medical staff to further effectively and accurately label fundus images and an apparatus using the same.

Non-patent document 1: Goodfellow, Ian J.; Pouget-Abadie, Jean; Mirza, Mehdi; Xu, Bing; Warde-Farley, David; Ozair, Sherjil; Courville, Aaron; Bengio, Yoshua (2014). "Generative Adversarial Networks"

Non-patent document 2: Ronneberger O., Fischer P., Brox T. (2015) U-Net: Convolutional Networks for Biomedical Image Segmentation. In: Navab N., Hornegger J., Wells W., Frangi A. (eds) Medical Image Computing and Computer-Assisted Intervention—MICCAI 2015. Lecture Notes in Computer Science, vol 9351. Springer, Cham

DETAILED DESCRIPTION

Technical Subject

The present disclosure is to provide the convenience in reading a fundus image by providing areas divided by applying anatomical characteristics using artificial intelligence.

Also, the present disclosure is to apply exclusive relationships between diseases to labeling items by selectively including logically appropriate items in a labeling system and to effectively arrange data by distinguishing a finding and diagnosis from each other.

Also, the present disclosure is to easily perform a section division by setting a section based on positional characteristics of major findings and structural characteristics of eyes and, particularly, automatically detecting positions of macula and optic disc.

Solution

Characteristic constitutions of the disclosure to accomplish the aforementioned objectives and to achieve characteristic effects of the disclosure are as follows:

According to an aspect of the present disclosure, there is provided a method of supporting reading of a fundus image of a subject, the method including: (a) acquiring, by a computing apparatus, or supporting another apparatus interacting with the computing apparatus to acquire the fundus image of the subject; (b) extracting, by the computing apparatus, or supporting the other apparatus to extract attribute information from the fundus image based on a machine learning model for extracting the attribute information of the fundus image; and (c) providing, by the computing apparatus, or supporting the other apparatus to provide the extracted attribute information to an external entity.

Desirably, the method may further include, (d) when evaluation information on the extracted attribute information or modification information in which the extracted attribute information is arbitrarily modified is acquired, updating, by the computing apparatus, or supporting the other apparatus to update the machine learning model based on the evaluation information or the modification information.

According to another aspect of the present disclosure, there is provided a method of supporting reading of a fundus image of a subject, the method including: (a) acquiring, by a computing apparatus, or supporting another apparatus interacting with the computing apparatus to acquire the fundus image of the subject; (b) performing, by the computing apparatus, at least one of (i) a process of generating or supporting the other apparatus to generate normality status information of the fundus image and (ii) a process of receiving or supporting the other apparatus to receive the normality status information from at least one user; (c) generating, by the computing apparatus, or supporting the other apparatus to generate section division information representing individual sections of the fundus image, and performing at least one of (i) a process of generating or supporting the other apparatus to generate finding information corresponding to the individual sections and (ii) a process of receiving or supporting the other apparatus to receive the finding information from the at least one user; (d) performing, by the computing apparatus, at least one of (i) generating or supporting the other apparatus to generate diagnostic information on the fundus image based on the finding information and (ii) a process of receiving or supporting the other apparatus to receive the diagnostic information corresponding to the fundus image and the finding information from the at least one user: and (e) storing or providing, by the computing apparatus, supporting the other apparatus to store or provide the finding information and the diagnostic information on the fundus image to an external entity.

According to another aspect of the present disclosure, there is provided a computer program stored in a non-transitory computer-readable storage medium including instructions to perform the method.

According to still another aspect of the present disclosure, there is provided a computing apparatus for supporting reading of a fundus image of a subject, the apparatus including: a communicator configured to acquire the fundus image of the subject, and a processor configured to extract or support another apparatus interacting through the communicator to extract attribute information from the fundus image based on a machine learning model for extracting the attribute information of the fundus image acquired through the communicator. The processor is configured to provide or support the other apparatus to provide the extracted attribute information to an external entity.

Desirably, when evaluation information on the extracted attribute information or modification information in which the extracted attribute information is modified is acquired through the communicator, the processor may be configured to update or support the other apparatus to update the machine learning model based on the evaluation information or the modification information.

According to still another aspect of the present disclosure, there is provided a computing apparatus for supporting reading of a fundus image of a subject, the apparatus including: a communicator including an input module configured to acquire the fundus image of the subject, and a processor including a discrimination module configured to perform at least one of (1-i) a process of generating or supporting another apparatus interacting through the communicator to generate normality status information of the fundus image and (1-ii) a process of receiving or supporting the other apparatus to receive the normality status information from at least one user through the communicator. The discrimination module is configured to generate or support the other apparatus to generate section division information representing individual sections of the fundus image, and the processor further includes: a finding input module configured to perform at least one of (2-i) a process of generating or supporting the other apparatus to generate finding information corresponding to the individual sections and (2-ii) a process of receiving or supporting the other apparatus to receive the finding information from the at least one user through the communicator: a diagnostic result input module configured to perform at least one of (3-i) a process of generating or supporting the other apparatus to generate diagnostic information on the fundus image based on the finding information and (3-ii) a process of receiving or supporting the other apparatus to receive the diagnostic information corresponding to the fundus image and the finding information from the at least one user through the communicator; and a storage and transmission module configured to store or provide or support the other apparatus to store or provide the finding information and the diagnostic information on the fundus image to an external entity through the communicator.

Effects

According to the present disclosure, it is possible to prevent logically and pathologically unnecessary or unreasonable reading, which is found in a conventional fundus image labeling method, and to effectively display a position corresponding to a finding using a section setting based on structural characteristics of an eye.

Also, according to the present disclosure, it is possible to effectively arrange data and accordingly easily acquire data for an artificial intelligence learning model. Also, it is possible to provide initial attribute information, for example, binocular distinguishing information, position information of macula and optic disc, vascular information, and cup-to-disc (C/D) ratio information, which is easily available for reading through pre-learned information.

Also, according to the present disclosure, since pathologically impossible reading is filtered out in a system, it is possible to prevent the medical staff from making a mistake. Also, since a learning model is continuously updated as the use experience of a user accumulates, it is possible to improve the accuracy.

For example, it is possible to save a time of the medical staff, to improve the quality of care, and to innovate a workflow in the medical field by enabling effective and accurate reading.

According to the present disclosure, since it is possible to use a fundus captured image conventionally used in a hospital as is, for example, an image acquired from a fundus capturing device and Picture Archiving and Communications System (PACS), a method of the present disclosure is not dependent on a computer operating system.

BRIEF DESCRIPTION OF DRAWINGS

Example embodiments of the present disclosure will be described in more in detail with reference to the following figures that are simply a portion of the example embodiments and those of ordinary skill in the art (hereinafter, "those skilled in the art") to which this disclosure pertains may readily acquire other figures based on the figures without an inventive work being made:

FIG. 1 illustrates a major concept of a convolutional neural network (CNN) as an example of a machine learning model according to the present disclosure;

FIG. 2 is a diagram illustrating an example of a computing apparatus configured to perform a method (hereinafter, a "fundus image reading supporting method") of supporting reading of a fundus image of a subject according to the present disclosure;

FIG. 3 is a diagram illustrating an example of a hardware and software architecture of a computing apparatus configured to perform a fundus image reading supporting method according to the present disclosure;

FIG. 4 illustrates an example of vascular information by separating only an image of vessels in an example embodiment of a fundus image reading supporting method according to the present disclosure;

FIG. 5 illustrates a conventional method of detecting central positions of optic disc and macula;

FIG. 6 illustrates an example of a machine learning model for detecting central positions of optic disc and macula in an example embodiment of a fundus image reading supporting method according to the present disclosure;

FIG. 7 illustrates an example of section division information representing sections of a fundus image extracted in an example embodiment of a fundus image reading supporting method according to the present disclosure;

FIG. 8 is a flowchart illustrating an example embodiment of a fundus image reading supporting method according to the present disclosure;

FIG. 9 is a flowchart illustrating another example embodiment of a fundus image reading supporting method according to the present disclosure;

FIGS. 10A to 10E illustrate examples of a user interface (UI) provided in the respective operations of the example embodiment of FIG. 9; and FIG. 11 illustrates an example of a Bayesian network as a single method of generating diagnostic information from finding information in the example embodiment of FIG. 9.

BEST MODE

The following detailed description of this disclosure is described with reference to the accompanying drawings in which specific example embodiments of the disclosure are illustrated as examples, to fully describe purposes, technical solutions, and advantages of the disclosure. The example embodiments are described in detail enough for those skilled in the art to carry out the disclosure.

Further, the term "training" or "learning" used throughout the detailed description and the claims refers to performing a machine learning through computing according to a procedure and it will be apparent to those skilled in the art that the term is not intended to refer to a mental action such as an educational activity of a human.

Also, the terms "comprises/includes" used throughout the detailed description and the claims and modifications thereof are not intended to exclude other technical features, additions, components, or operations. Those skilled in the art may clearly understand a portion of other purposes, advantages, and features of the disclosure from this specification and another portion thereof from implementations of the disclosure. The following examples and drawings are provided as examples only and not to limit the disclosure.

Further, the disclosure may include any possible combinations of example embodiments described herein. It should be understood that, although various example embodiments differ from each other, they do not need to be exclusive. For example, a specific shape, structure, and feature described herein may be implemented as another example embodiment without departing from the spirit and scope of the disclosure. Also, it should be understood that a position or an arrangement of an individual component of each disclosed example embodiment may be modified without departing from the spirit and scope of the disclosure. Accordingly, the following detailed description is not to be construed as being limiting and the scope of the disclosure, if properly described, is limited by the claims, their equivalents, and all variations within the scope of the claims. In the drawings, like reference numerals refer to like elements throughout.

Unless the context clearly indicates otherwise, the singular forms "a," "an," and "the," are intended to include the plural forms as well. Also, when description related to a known configuration or function is deemed to render the present disclosure ambiguous, the corresponding description is omitted.

Hereinafter, example embodiments of the disclosure are described in detail with reference to the accompanying drawings such that those skilled in the art may easily perform the present disclosure.

FIG. 1 illustrates a major concept of a convolutional neural network (CNN) as an example of a machine learning model according to the present disclosure.

Referring to FIG. 1, in a machine learning model used herein, a deep neural network model may be briefly described to be in a form in which artificial neural networks are stacked in multiple layers. That is, a deep structured neural network may be represented as a deep neural network or a DNN that is a network in a deep structure, and, referring to FIG. 1, may be trained using a method of automatically learning features of vital signs and relationships between the vital signs through learning of a large amount of data in a structure that includes a multilayered network and, through this, reducing an error of a prediction accuracy of a target function, that is, fatal symptoms. It is also expressed as a concatenation between nerve cells of the human brain and the deep neural network (DNN) is becoming a next generation model of artificial intelligence (AI).

FIG. 2 is a diagram illustrating an example of a computing apparatus configured to perform a fundus image reading supporting method according to the present disclosure.

Referring to FIG. 2, a computing apparatus 200 according to an example embodiment of the present disclosure includes a communicator 210 and a processor 220, and may directly or indirectly communicate with an external computing apparatus (not shown) through the communicator 210.

In detail, the computing apparatus 200 may achieve a desired system performance using a combination of typical computer hardware (e.g., an apparatus including a computer processor, a memory, a storage, an input device and an output device, device which can include components of other existing computing apparatuses, etc.); an electronic communication apparatus such as a router, a switch, etc.; an electronic information storage system such as a network-attached storage (NAS) and a storage area network (SAN)) and computer software (i.e., instructions that enable a computing apparatus to function in a specific manner).

The communicator 210 of the computing apparatus 200 may transmit and receive a request and a response with another interacting computing apparatus. As an example, the request and the response may be implemented using the same transmission control protocol (TCP) session. However, it is provided as an example only. For example, the request and the response may be transmitted and received as a user datagram protocol (UDP) datagram. In addition, in a broad sense, the communicator 210 may include a keyboard, a mouse, and other external input devices to receive a command or an instruction.

Also, the processor 220 of the computing apparatus 200 may include a hardware configuration, such as a micro processing unit (MPU), a central processing unit (CPU), a cache memory, a data bus, and the like. Also, the processor 220 may further include a software configuration of an application that performs a specific objective, an operating system (OS), and the like.

FIG. 3 is a diagram illustrating an example of a hardware and software architecture of a computing apparatus configured to perform a fundus image reading supporting method according to the present disclosure.

Describing a method and a configuration of an apparatus according to the present disclosure with reference to FIG. 3, the computing apparatus 200 may include an image acquisition module 310 as a component. It will be apparent to those skilled in the art that the image acquisition module 310 may be configured through, for example, the communicator 210 included in the computing apparatus 200, or through interaction between the communicator 210 and the processor 220.

The image acquisition module 310 may acquire a fundus image of a subject. For example, although the fundus image may be acquired from a fundus image capturing device or Picture Archiving and Communications System (PACS) of the subject, it is provided as an example only. Many fundus images correspond to intermediate images and may correspond to 7-segment montage of diabetic accordingly.

Also, the acquired fundus image may be forwarded to a discrimination module 320. The discrimination module 320 extracts attribute information of the fundus image based on a machine learning model.

For example, the attribute information of the fundus image may include (i) vascular information separately representing only an image of optic nerve vessels included in the fundus image, (ii) binocular distinguishing information representing whether the fundus image is a left-eye image or a right-eye image, (iii) position information representing a position of at least one of macula and optic disc included in the fundus image, (iv) section division information representing sections of the fundus image, (v) information of a cup-to-disc (C/D) ratio according to the fundus image, and the like.

First, in the case of the vascular information, the machine learning model of the discrimination module 320 may include a convolutional neural network (CNN) and a generative adversarial network (GAN).

According to the paper regarding the GAN, non-patent document 1: [Goodfellow, Ian J.; Pouget-Abadie, Jean; Mirza, Mehdi; Xu, Bing; Warde-Farley, David; Ozair, Sherjil; Courville, Aaron; Bengio, Yoshua (2014). "Generative Adversarial Networks"], a generator of the GAN is configured to generate data similar to true data to deceive a discriminator, such that the discriminator may determine the similar data as the true data, and the discriminator is configured to discriminate the true data from the generated similar data. During progress of learning by the GAN, each of the generator and the discriminator updates a network weight to achieve each corresponding purpose. Accordingly, after sufficient learning, the generator may generate data similar to true data and a discrimination rate by the discriminator may converge theoretically to 0.5. Therefore, since the generator sufficiently trained by the GAN may generate data close to true data, a data imbalance issue in machine learning may be solved.

If learning proceeds through sufficient iterations by using the CNN and the GAN together, the image of optic nerve vessels may be extracted based on the machine learning model. FIG. 4 illustrates an example of vascular information by separating only an image of vessels in an example embodiment of a fundus image reading supporting method according to the present disclosure.

Second, in the case of the laterality information, the machine learning model may include a segmentation network. The binocular distinguishing information of the fundus image may be extracted based on a shape of the optic disc of the fundus image and driving of vessels coming from the optic disc by identifying at least one of the shape of the optic disc and driving of the vessels based on the machine learning model.

In detail, in the case of extracting the laterality information, it may be impossible to determine whether the corresponding fundus image is a left-eye image or a right-eye image only with a position of the optic disc. Therefore, to improve the discrimination accuracy thereof, learning of the machine learning model is performed by using the fundus image that is impossible to determine only with the position of the optic disc as learning data. In the case of the right eye, an image captured at ophthalmology is generally focused on the center thereof and the optic disc is on the right accordingly. In contrast, the learning data includes an image in which the optic disc is on the left or on an inferior side despite the right eye. In this manner, the accuracy of laterality may be improved.

A z-score (standardization score) of an individual channel of the fundus image is calculated and used as an input of the CNN. The z-score may be represented by the following Equation 1.

$$z_{x,y} = \frac{I_{x,y} - \mu}{\sigma} \quad \text{[Equation 1]}$$

Using the z-score, it is possible to discriminate both eyes from each other based on shape information completely included in an image without being affected by intensity or contrast of the fundus image. The following examples of a segmentation network may be used herein.

conv(2)-conv-maxpool(2)-conv(2)-conv-conv-maxpool(2)-conv-conv-conv-maxpool(22)-conv-conv-conv-maxpool(2)-conv-conv-dense(256)-dense(1)

Here, input data is a red, green, blue (RGB) image converted using the z-score of 512×512 and a stride of "conv" and "maxpool" is represented as (x). Also, "selu" is used for an activation function, sigmoid is used for a last "dense" layer, and binary cross entropy is used for a loss function.

Third, in the case of the position information, the machine learning model may include a segmentation network and a position of at least one of the macula and the optic disc may be extracted based on the machine learning model.

FIG. 5 illustrates a conventional method of detecting central positions of optic disc and macula. Here, the optic disc and the macula function as reference points used to read a fundus image. In the related art, a position of the macula is detected through optical coherence tomography (OCT) and the optic disc brightly and clearly appears in the fundus image and a position of the optic disc may be relatively easily determined accordingly. Therefore, the optic disc is detected from the fundus image. Dissimilar to the conventional method, the present disclosure may detect all of positions of the macula and the optic disc from the fundus image without using an OCT captured image.

FIG. 6 illustrates an example of a machine learning model for detecting central positions of optic disc and macula in an example embodiment of a fundus image reading supporting method according to the present disclosure.

In detail, when detecting central positions of the optic disc and the macula, medical experts may proceed with learning of the machine learning model using labeling (in detail, capturing position coordinates) as learning data with respect to a fundus image with a lesion as well as a normal fundus image. As an example of the machine learning model, as disclosed in non-patent document 2: [Ronneberger O., Fischer P., Brox T. (2015) U-Net: Convolutional Networks for Biomedical Image Segmentation. In: Navab N., Hornegger J., Wells W., Frangi A. (eds) Medical Image Computing and Computer-Assisted Intervention—MICCAI 2015. Lecture Notes in Computer Science, vol 9351. Springer, Cham], a depth concatenation scheme used for U-Net that uses a padding form, a number of layers, and a depth of an individual layer as parameters may be used. A form of such a network is illustrated in detail in FIG. 6.

Referring to FIG. 6, in this network, z-score is calculated for each individual channel and a segmented vessel is used as input with respect to a 640×640 RGB image, batch-normalization used, and binary cross entropy is used as a loss function. In FIG. 6, "Operations" represents an operation of an individual block, "Skip-connected" represents a depth concat layer in the U-Net, and "Upsample" represents that each of a length and a width is doubled using bilinear interpolation.

Fourth, in the case of the section division information, the machine learning model includes a segmentation network and positions of the macula and the optic disc are extracted based on the machine learning model. Accordingly, the section division information for dividing the fundus image into individual sections may be extracted based on a central position of the macula and a central position of the optic disc. Desirably, the individual sections may include at least three and may be variously configured depending on the necessity of the medical staff.

As an example embodiment of dividing the fundus image into the individual sections, the individual sections may include a macula area, a superior disc area, an inferior disc area, a temporal area, a superotemporal area, an inferotemporal area, a superonasal area, and an inferonasal area.

FIG. 7 illustrates an example of section division information representing sections of a fundus image extracted in the example embodiment.

Referring to FIG. 7, the macula area may be an interior area of a macula center circle having a radius of k1*d with respect to predetermined k1 that satisfies 0<k1≤1 if a distance between a central position of the macula and a central position of the optic disc is d, and having the central position of the macula as a center.

Also, the superior disc area may be a superior area among areas divided from an optic disc area that is an interior area of an optic disc center circle having a radius of k2*d with respect to the distance d and predetermined k2 that satisfies 0<k2≤1 and having the central position of the optic disc as a center by a straight line $l_1$ that passes the central position of the macula and the central position of the optic disc.

Also, the inferior disc area may be an inferior area among the areas divided from the optic disc area by the straight line L.

Also, the superonasal area may be an area excluding the superior disc area from a superior area away from the macula among areas divided by the straight line $l_1$ and a straight line $l_2$ that passes the central position of the optic disc perpendicularly relative to the straight line $l_1$.

Also, the inferonasal area may be an area excluding the inferior disc area from an inferior area away from the macula among the areas divided by the straight line $l_1$ and the straight line $l_2$.

Also, the temporal area may be an area excluding the macula area from an area including the straight line $l_1$ among areas divided by the macular center circle and two half lines $l_3$ and $l_4$ parallel to the straight line $l_1$ and in contact with the macula center circle and extending away from the optic disc.

Also, the superotemporal area may be an area excluding the superior disc area, the macula area, and the temporal area from a superior area close to the macula among the areas divided by the straight line $l_1$ and the straight line $l_2$.

Also, the inferotemporal area may be an area excluding the inferior disc area, the macula area, and the temporal area from an inferior area close to the macula among the areas divided by the straight line $l_1$ and the straight line $l_2$.

Desirably, k1=⅔ and k2=⅖ and a result thereof is illustrated in FIG. 7.

Fifth, in the case of the C/D ratio information, the machine learning model may include a segmentation network and the C/D ratio may be extracted by identifying the optic disc and the optic cup based on the machine learning model.

In the clinical fundus reading, the optic cup refers to a portion of the blood vessels connected to the brain inside the optic disc. Since the optic nerve bundle enters between the optic cup and the optic disc, a high C/D ratio may damage the optic nerve. This may be a basis for suspecting glaucoma.

The segmentation network model used herein may be, for example, a model in which a convolution block in a visual geometry group (VGG) network form is stacked and a fully connected layer is connected to the convolution block. Through this, glaucoma may be automatically read at high accuracy (ROC_AUC 0.8617 or more).

As described above, learning of the machine learning model used for the discrimination module 320 may be performed in the discrimination module 320 and may be performed through a separate learning module 330.

When attribute information on an individual fundus image is extracted based on the machine learning model, the attribute information may be stored or provided to an external entity, or may be provided to another apparatus (not shown) interacting with the computing apparatus 200 through a storage and transmission module 340.

Referring again to FIG. 3, a result input module 350 configured to acquire evaluation information on the extracted attribute information and modification information in which the extracted attribute information is arbitrarily modified and an update module 360 configured to update the machine learning model based on the evaluation information or the modification information may be further provided as components of the computing apparatus 200. The above modules 310 through 360 may be implemented by the communicator 210 and the processor 220.

In detail, the result input module 350 may further include a finding input module 352 (not shown) and a diagnostic result input module 354 (not show) in a second example embodiment of a fundus image reading supporting method, which is described below.

Hereinafter, a first example embodiment of a fundus image reading supporting method according to the present disclosure is described with reference to FIG. 8. FIG. 8 is a flowchart illustrating an example of a fundus image reading supporting method according to a first example embodiment of the present disclosure.

Referring to FIG. 8, the fundus image reading supporting method according to the example embodiment includes operation S810 of acquiring, by the image acquisition module 310 implemented by the communicator 210 of the computing apparatus 200, or supporting another apparatus (not shown) interacting with the computing apparatus 200 to acquire the fundus image of the subject.

Also, the fundus image reading supporting method according to the example embodiment of the present disclosure includes operation S820 of extracting, by the discrimination module 320 implemented by the processor 220 of the computing apparatus 200, or supporting the other apparatus to extract attribute information from the fundus image based on a machine learning model for extracting the attribute information of the fundus image, and operation S830 of providing, by the storage and transmission module 340 implemented by the processor 220 and communicator 210 of the computing apparatus 200, or supporting the other apparatus to provide the extracted attribute information to an external entity.

Here, the external entity may include a user and a manager of the computing apparatus 200, a medical expert in charge of the subject, and the like. In addition, any entity capable of reading the fundus image may be included.

Also, prior to performing the fundus image reading supporting method, an operation (not shown) of pre-training the machine learning model needs to be performed. To this end, the learning module 330 may be executed by the processor 220.

For example, the learning module 330 may train the machine learning model by using individual fundus images for a plurality of fundus images and labeling data thereof as learning data.

In the example embodiment, it is possible to support reading of a fundus image based on the pre-trained machine learning model. Therefore, if evaluation information or modification information of the extracted attribute information is used again as data to retrain the machine learning model, the accuracy of the machine learning model may be further improved. Accordingly, the fundus image reading supporting method according to the example embodiment of the present disclosure may further include operation S840 of acquiring, by the apparatus 220, evaluation information of the extracted attribute information or modification information in which the extracted attribute information is arbitrarily modified through the result input module 350 and updating or supporting the other apparatus to update the machine learning model based on the evaluation information or the modification information through the update module 360. Here, since fundus images and labeling data not considered for previous learning are additionally considered and an error found in the previous learning is correctable, the accuracy of the machine learning model may be improved and accordingly, the performance of the machine learning may be continuously improved as data accumulates.

Here, the evaluation information and the modification information may be provided from the external entity, such as, for example, the medical expert and the like.

Hereinafter, a second example embodiment of a fundus image reading supporting method according to the present disclosure is described with reference to FIG. 9 and FIGS. 10A to 10E.

FIG. 9 is a flowchart illustrating an example of the second example embodiment of the fundus image reading supporting method according to the present disclosure, and FIGS. 10A to 10E illustrate examples of a user interface (UI) provided in the respective operations of the example embodiment of FIG. 9.

Referring to FIG. 9, the fundus image reading supporting method according to the second example embodiment includes operation S910 of acquiring, by the image acquisition module 310 implemented by the communicator 210 of the computing apparatus 200, or supporting another apparatus interacting with the computing apparatus 200 to acquire the fundus image of the subject.

Referring to FIG. 10A, in operation S910, at least one of an identification (LD) number, an age, and a sex of the subject and binocular distinguishing information of the fundus image may be provided to a user, that is, a reader, for convenience of the user. Also, reading may be performed by a plurality of users. A plurality of readings may be performed with respect to the single fundus image by selecting at least one user supporting reading of the fundus image according to the method disclosed herein from among Kn users included in an n-th user group among a total of M user groups. Through this, cross-verification may be performed with respect to labeling data as a reading result.

Referring again to FIG. 9, the fundus image reading supporting method according to the example embodiment further include operation S920 of performing, by the discrimination module 320 implemented by the processor 220 of the computing apparatus 200, at least one of (i) a process of generating or supporting the other apparatus to generate normality status information of the fundus image and (ii) a process of receiving or supporting the other apparatus to receive the normality status information from at least one user.

Referring to FIG. 10B, the normality status information of the fundus image may be one of abnormal fundus and normal fundus. For example, if the normal fundus is selected, the method of the example embodiment may be completed with respect to the corresponding fundus image and a subsequent fundus image may be loaded.

If quality of the fundus image needs to be evaluated prior to operation S920, the fundus image reading supporting method may further include operation S915 (not shown) of performing, by the discrimination module 320, at least one of (i) a process of generating or supporting the other apparatus to generate image quality information evaluating quality of the fundus image and (ii) a process of receiving or supporting the other apparatus to receive the image quality information from the at least one user.

Referring to FIG. 10A, the image quality information may include at least one of good, media opacity, small pupil/defocusing, and ungradable. For example, if ungradable is selected, the method of the example embodiment may be completed with respect to the corresponding fundus image and a subsequent fundus image may be loaded.

After performing operation S920, the fundus image reading supporting method further includes operation S930 of generating, by the processor 220 of the computing apparatus 200, or supporting the other apparatus to generate section division information representing individual sections of the fundus image through the discrimination module 320, and performing at least one of (i) a process of generating or supporting the other apparatus to generate finding information corresponding to the individual sections and (ii) a process of receiving or supporting the other apparatus to receive the finding information from the at least one user through the communicator 210, through the finding input module 352.

Referring to FIG. 10C, the finding information corresponding to the individual sections of the fundus image may include hemorrhage, hard exudate, cotton wool spot, drusen & drusenoid deposits, and retinal pigmentary change, and, without being limited thereto, may include macular hole, vascular abnormality, membrane, fluid accumulation, chroioretinal atrophy/scar, choroidal lesion, myelinated nerve fiber, RNFL defect, glaucomatous disc change, non-glaucomatous disc change, other findings or artifact, and the like.

Also, the fundus image reading supporting method according to the example embodiment further includes operation S940 of performing, by the processor 220 of the computing apparatus 200, at least one of (i) generating or supporting the other apparatus to generate diagnostic information on the fundus image based on the finding information and (ii) a process of receiving or supporting the other apparatus to receive the diagnostic information corresponding to the fundus image and the finding information from the at least one user, through the diagnostic result input module 354.

Referring to FIG. 10D, the diagnostic information may include dry AMD, wet AMD, early DR, advanced DR, CRVO, BRVO/hemi-CRVO, epiretinal membrane, macular Hole, other retinal/choroidal diseases/findings, glaucoma suspect, and other disc diseases/findings, and floaters/artifacts suspect.

As described above, not only a single piece of but also a plurality of pieces of diagnostic information may be selected. Here, an exclusive relationship is present between such diagnostic information. Selection of dry AMD and selection of wet AMD are mutually exclusive. Also, selection of early DR and selection of advanced DR are mutually exclusive, and selection of CRVO and selection of BRVO/hemi-CRVO are mutually exclusive. This is to prevent logically and pathologically unnecessary or unreasonable reading.

As described above, a deep learning scheme, such as CNN, may be applied to a machine learning model that generates diagnostic information based on finding information, and other statistical methods, known in the art, such as, for example, a Bayesian network, may be employed.

FIG. 11 illustrates an example of a Bayesian network as a single method of generating diagnostic information from finding information in the example embodiment of FIG. 9.

The Bayesian network may be used to probabilistically infer final diagnostic information from an input value which is finding information. Connections between the respective nodes illustrated in FIG. 11 as an example correspond to probabilistic values thereof.

Also, the fundus image reading supporting method according to the example embodiment of the present disclosure further includes operation S950 of storing or providing, by the processor 220, supporting the other apparatus to store or provide the finding information and the diagnostic information on the fundus image to an external entity through the storage and transmission module 340.

Referring to a user interface (UI) of FIG. 10E, in operation S950, by providing the finding information and the diagnostic information on the fundus image to an ophthalmologist in response to a selection from at least one user, it is possible to support the ophthalmologist to modify the finding information and the diagnostic information.

Similar to the first example embodiment, the fundus image reading supporting method according to the second example embodiment may further include operation S960 (not shown) of acquiring evaluation information related to finding information and diagnostic information or modification information in which finding information and diagnostic information determined by the machine learning model are arbitrarily modified through the finding input module 352 or the diagnostic result input module 354 and updating or supporting the other apparatus to update the machine learning model based on the evaluation information or the modification information through the update module 360. Here, since an error found in previous learning may be corrected, the accuracy of the machine learning model may be improved and accordingly, the performance of machine learning may be continuously improved as data accumulates.

As described above, compared to the related art in which medical experts read fundus images one by one depending on their experience or knowledge, the example embodiments disclosed herein may save a time of the medical staff, improve the quality of care, and innovate a workflow in the medical field by enabling effective and accurate reading.

One of ordinary skill in the art may easily understand that the present disclosure may be implemented through combination of hardware and software or hardware only based on the example embodiments. Targets of technical solutions of the disclosure or portions contributing to the arts may be configured in a form of program instructions performed by various computer components and stored in non-transitory computer-readable storage media. The media may include, alone or in combination with the program instructions, data files, data structures, and the like. The program instructions recorded in the media may be specially designed and configured for the disclosure, or may be known to those skilled in the art of computer software. Examples of the media may include magnetic media such as hard disks, floppy disks, and magnetic tapes; optical media such as CD-ROM and DVDs; magneto-optical media such as floptical disks; and hardware devices that are specially configured to store and perform program instructions, such as ROM, RAM, flash memory, and the like. Examples of program instructions may include a machine code, such as produced by a compiler and higher language code that may be executed by a computer using an interpreter.

The described hardware devices may be to act as one or more software modules in order to perform the operations of the above-described example embodiments, or vice versa. The hardware devices may include a processor, such as, for example, a CPU and a GPU, configured to be combined with a memory such as ROM/RAM configured to store program instructions and to execute the instructions stored in the memory, and may include a communicator capable of transmitting and receiving a signal with an external device. In addition, the hardware devices may include a keyboard, a mouse, and an external input device for receiving instructions created by developers.

While this disclosure is described with reference to specific matters such as components, some example embodiments, and drawings, they are merely provided to help general understanding of the disclosure and this disclosure is not limited to the example embodiments. It will be apparent to those skilled in the art that various alternations and modifications in forms and details may be made from the example embodiments.

Therefore, the scope of this disclosure is not defined by the example embodiments, but by the claims and their equivalents, and all variations within the scope of the claims and their equivalents are to be construed as being included in the disclosure.

Such equally or equivalently modified example embodiments may include, for example, logically equivalent methods capable of achieving the same results as those acquired by implementing the method according to the present disclosure.

What is claimed is:

1. A method of outputting attribute information related to reading of a fundus image of a subject by a computing apparatus, the method comprising:
   acquiring the fundus image of the subject;
   extracting the attribute information including position information on a macular center and an optic disc center from the fundus image based on a machine learning model for extracting the attribute information of the fundus image,
   wherein the attribute information further includes area division information for the fundus image divided into a plurality of areas based on (i) a first line that passes the macular center and the optic disc center and (ii) a second line that passes the optic disc center perpendicularly relative to the first line;
   outputting the extracted attribute information, and outputting, by using the machine learning model, diagnostic information including diagnostic results for each of the plurality of areas.

2. The method of claim 1, further comprising:
when evaluation information on the extracted attribute information or modification information in which the extracted attribute information is arbitrarily modified is acquired, updating the machine learning model based on the evaluation information or the modification information.

3. The method of claim 1, wherein the attribute information of the fundus image further comprises at least one of binocular distinguishing information representing whether the fundus image is a left-eye image or a right eye image, vascular information separately representing an image of optic nerve vessels included in the fundus image, and information of a cup-to-disc (C/D) ratio according to the fundus image,
wherein the plurality of areas include a macula area and an optic disc area determined based on a first distance between the macular center and the optic disc center.

4. The method of claim 3, wherein, when the attribute information is the vascular information, the machine learning model comprises a convolutional neural network (CNN) and a generative adversarial network (GAN), and the image of optic nerve vessels is extracted based on the machine learning model.

5. The method of claim 3, wherein, when the attribute information is the laterality information, the machine learning model comprises a segmentation network, and the binocular distinguishing information of the fundus image is extracted based on a shape of the optic disc area of the fundus image and driving of vessels coming from the optic disc area by identifying at least one of the shape of the optic disc area and driving of the vessels based on the machine learning model.

6. The method of claim 1, wherein the plurality of areas include a macular area and an optic disc area,
wherein the macula area is determined based on a circular area having a first radius calculated by multiplying a first distance between the macular center and the macular center by K1 with the macular center as a center,
wherein the optic disc area is determined based on a circular area having a second radius calculated by multiplying the first distance by K2 with the optic disc center as a center,
wherein K1 satisfies 0<k1≤1, and K2 satisfies 0<k2≤1, and
wherein a sum of K1 and K2 is greater than 1.

7. The method of claim 6, wherein the area division information further comprises a superior disc area, an inferior disc area, a temporal area, a superotemporal area, an inferotemporal area, a superonasal area, and an inferonasal area,
wherein the superior disc area is a superior area among areas divided from the optic disc area by the first line,
wherein the inferior disc area is an inferior area among the areas divided from the optic disc area by the first line,
wherein the superonasal area is an area excluding the superior disc area from a superior area away from the macula area among areas divided by the first line and the second line,
wherein the inferonasal area is an area excluding the inferior disc area from an inferior area away from the macula area among the areas divided by the first line and the second line, wherein the temporal area is an area excluding the macula area from an area including the first line among areas divided by the macular center circle and two half lines parallel to the first line and in contact with the macula center circle and extending away from the optic disc area,
wherein the superotemporal area is an area excluding the superior disc area, the macula area, and the temporal area from a superior area close to the macula area among the areas divided by the first line and the second line, and
wherein the inferotemporal area is an area excluding the inferior disc area, the macula area, and the temporal area from an inferior area close to the macula area among the areas divided by the first line and the second line.

8. The method of claim 3, wherein, when the attribute information includes the C/D ratio information, the machine learning model comprises a segmentation network, and the C/D ratio is extracted by identifying the optic disc area and an optic cup based on the machine learning model.

9. A non-transitory computer-readable storage medium storing instructions that, when executed by a processor, cause the processor to perform the method of claim 1.

10. A method of supporting reading of a fundus image of a subject by a computing apparatus, the method comprising:
acquiring the fundus image of the subject;
generating normality status information of the fundus image and receiving the normality status information from at least one user;
generating area division information for the fundus image divided into a plurality of areas based on (i) a first line that passes a macular center and an optic disc center and (ii) a second line that passes the optic disc center perpendicularly relative to the first liner;
generating, by using the machine learning model, diagnostic information including diagnostic results for each of the plurality of areas by using the machine learning model; and
storing or providing the diagnostic information on the fundus image to an external entity,
wherein the macular center and the optic disc center are extracted from the fundus image using the machine learning model for extracting attribute information of the fundus image.

11. The method of claim 10, further comprising:
generating image quality information evaluating quality of the fundus image and receiving the image quality information from the at least one user.

12. The method of claim 10, further comprising:
providing at least one of an identification (ID) number, an age, and a sex of the subject, and binocular distinguishing information of the fundus image to the at least one user.

13. The method of claim 10, wherein a plurality of readings is performed with respect to the single fundus image by selecting the at least one user from among Kn users included in an n-th user group among a total of M user groups.

14. A computing apparatus for outputting attribute information related to reading of a fundus image of a subject, the computing apparatus comprising:
a communicator configured to acquire the fundus image of the subject; and
a processor,
wherein the processor is configured to:

extract the attribute information including position information on a macular center and an optic disc center from the fundus image based on a machine learning model for extracting the attribute information of the fundus image acquired through the communicator, wherein the attribute information further includes area division information for the fundus image divided into a plurality of areas based on (i) a first line that passes the macular center and the optic disc center and (ii) a second line that passes the optic disc center perpendicularly relative to the first line;

output the extracted attribute information; and output, by using the machine learning model, diagnostic information including diagnostic results for each of the plurality of areas.

15. The computing apparatus of claim 14, wherein, when evaluation information on the extracted attribute information or modification information in which the extracted attribute information is modified is acquired through the communicator, the processor is configured to update the machine learning model based on the evaluation information or the modification information.

16. The computing apparatus of claim 14, wherein the attribute information of the fundus image further comprises at least one of binocular distinguishing information representing whether the fundus image is a left-eye image or a right eye image, vascular information separately representing an image of optic nerve vessels included in the fundus image, and information of a cup-to-disc (C/D) ratio according to the fundus image, wherein the plurality of areas include a macula area and an optic disc area determined based on a first distance between the macular center and the optic disc center.

* * * * *